United States Patent
Zheng et al.

(10) Patent No.: US 8,600,475 B2
(45) Date of Patent: Dec. 3, 2013

(54) RELAXATION-CORRECTED ECG-TRIGGERING AND NAVIGATOR-GATING TECHNIQUE

(75) Inventors: Shaokuan Zheng, Shrewsbury, MA (US); Mitchell Albert, Boston, MA (US)

(73) Assignee: University of Massachusetts, Boston, MA (US)

( * ) Notice: Subject to any disclaimer, the term of this patent is extended or adjusted under 35 U.S.C. 154(b) by 290 days.

(21) Appl. No.: 13/080,281

(22) Filed: Apr. 5, 2011

(65) Prior Publication Data
US 2012/0259202 A1  Oct. 11, 2012

(51) Int. Cl.
*A61B 5/055* (2006.01)
(52) U.S. Cl.
USPC .......................... 600/413; 600/410
(58) Field of Classification Search
USPC .................. 600/410, 413; 324/307, 309
See application file for complete search history.

(56) References Cited

U.S. PATENT DOCUMENTS

2012/0232378 A1* 9/2012 Messroghli .......... 600/413

* cited by examiner

*Primary Examiner* — Ruth S Smith
(74) *Attorney, Agent, or Firm* — Milstein Zhang & Wu LLC; Joseph B. Milstein (57) ABSTRACT

A system and method for recording magnetic resonance images with reduced relaxation-related artifacts. The system and method improve the conventional methods for acquiring magnetic resonance images of in vivo tissue by augmenting the procedures for eliminating artifacts caused by motion with procedures for eliminating artifacts caused by spin of the magnetic resonance-active nuclei in the specimen of interest. One procedure to eliminate such spin inhomogeneities is to require a delay defined by the time $N*T_1$, where N is a numerical value greater than or equal to 5 and $T_1$ is the characteristic time constant for decay of spins back to the equilibrium longitudinal state. Another procedure uses a value of N less than 5.

16 Claims, 5 Drawing Sheets

PRIOR ART

PRIOR ART

FIG. 2A   FIG. 2B

Normal Gating Method   Modified Gating Method

FIG. 2C   FIG. 2D

PRIOR ART

RELAXATION-CORRECTED ECG-TRIGGERING AND NAVIGATOR-GATING TECHNIQUE

FIELD OF THE INVENTION

The invention relates to NMR imaging systems and methods in general and particularly to a Multi Two Dimensional (M2D) NMR system and method.

BACKGROUND OF THE INVENTION

When investigators perform in vivo MR imaging of thoracic organs, movement of tissues is caused by the cycle of muscular contractions of the atria and ventricles of the heart, and by the cycle of respiration created by movement of the diaphragm, even while the subject is nominally in a resting condition. These two sources of movement can cause motion artifacts in MR images. Previous work provided methodologies to reduce or eliminate artifacts in image acquisition caused by cardiac and respiratory movements. See for example, Wang Y, Rossman P J, Grimm R C, Riederer S J, Ehman R L. Navigator-echo-based real-time respiratory gating and triggering for reduction of respiration effects in Coronary Artery Disease 437 three-dimensional coronary MR angiography. Radiology 1996; 198:55-60; Danias P G, McConnell M V, Khasgiwala V C, Chuang M L, Edelman R R, Manning W J. Prospective navigator correction of image position for coronary MR angiography. Radiology 1997;203: 733-736; McConnell M V, Khasgiwala V C, Savord B J et al. Prospective adaptive navigator correction for breath-hold MR coronary angiography. Magn Reson Med 1997;37:148-152; McConnell M V, Khasgiwala V C, Savord B J, Chen M H, Chuang M L, Edelman R R, Manning W J. Comparison of respiratory suppression methods and navigator locations for MR coronary angiography. AJR Am J Roentgenol 1997;168: 1369-1375; and Kotys M S, Herzka D A, Vonken E J, Ohayon J, Heroux J, Gharib A M, Stuber M, Pettigrew R I. Profile order and time-dependent artifacts in contrast-enhanced coronary MR angiography at 3T: origin and prevention. Magn Reson Med. 2009 August; 62(2):292-9.

Cardiac-Gating Technique

The effect of cardiac movement can be reduced by using ECG data collected from the subject to trigger MR image acquisition. By using ECG data to trigger image acquisition, acquisition can be acquired only when the heart is in diastole. This technique is called cardiac triggering, and serves to reduce the cardiac motion artifacts that would otherwise be observed.

Diaphragm-Gating Technique

Respiratory movement is controlled for with the so-called navigator technique. In the navigator technique, the position of the top of the diaphragm is monitored with a navigator "pencil beam" radio-frequency (RF) pulse that measures the location of the dome of the right side of the diaphragm. Using this information on diaphragm position, MR image acquisition is only performed when the diaphragm is in a predetermined window of location. Specifically, in the conventional navigator gating method, a free navigator is performed to get the most stable and consistent diaphragm position. The acquired data is only accepted when the diaphragm is within the navigator window. If there is motion outside of the navigator window, the scanner software rejects the acquired data. Additional data samples to make up for the rejected data are then acquired until the data are sampled when the diaphragm is in position within the navigator window.

When the ECG-triggering and navigator-gating techniques are combined, they can control for the movements of the cardiac and respiratory cycles. However, they do not control for another source of artifact, namely, that resulting from variation in spin condition of nuclei in the tissues being imaged.

When an RF signal acquisition step (also referred to as a "shot" or as a "normal shot") is conducted, it affects the condition of the spin of nuclei in the tissues being imaged, causing a deviation from the relaxed position. A "shot" can be a series of RF pulses in the case of a fast imaging sequence. If the spin of nuclei is not fully relaxed when the next shot is conducted, an artifact is created. For example, if an M2D and single-shot turbo field echo (TFE) pulse sequence, combined with the normal ECG-triggering and navigator-gating techniques, is used to acquire sagittal heart images, the intensity of different slices is different, which results in a severe "banding artifact" once the transverse or coronal images are reconstructed from the sagittal images. This banding artifact impairs the ability of clinicians to accurate diagnose heart disease. In the M2D and single-shot turbo field echo (TFE) pulse sequence method, multiple image slices are excited one after the other and each slice is acquired within one heart beat.

Also known in the prior art is Pines et al., U.S. Pat. No. 7,061,237, issued Jun. 13, 2006, which is said to disclose an apparatus and method for remote NMR/MRI spectroscopy having an encoding coil with a sample chamber, a supply of signal carriers, preferably hyperpolarized xenon and a detector allowing the spatial and temporal separation of signal preparation and signal detection steps. This separation allows the physical conditions and methods of the encoding and detection steps to be optimized independently. The encoding of the carrier molecules may take place in a high or a low magnetic field and conventional NMR pulse sequences can be split between encoding and detection steps. In one embodiment, the detector is a high magnetic field NMR apparatus. In another embodiment, the detector is a superconducting quantum interference device. A further embodiment uses optical detection of Rb—Xe spin exchange. Another embodiment uses an optical magnetometer using non-linear Faraday rotation. Concentration of the signal carriers in the detector can greatly improve the signal-to-noise ratio.

There is a need for systems and methods for providing improved in vivo magnetic resonance images of subjects.

SUMMARY OF THE INVENTION

According to one aspect, the invention features an improvement in a magnetic resonance imaging system having a computer-based control apparatus that controls the timing of the taking of magnetic resonance images based on a muscular state of a body part of a living subject. The improvement comprises a set of instructions recorded on a machine-readable medium, the set of instructions when operating configured to control the operation of the system in response to two conditions to provide two mutually exclusive outcomes, so as to permit the taking of a magnetic resonance image (a "shot") when both a muscular condition is within an acceptable range and when, for all shots after a first shot, a time elapsed since the last shot was taken is at least $N * T_1$, where $T_1$ is a time constant representative of a decay rate for a specimen of interest in a magnetic resonance process and N represents a numerical value greater than one, and $N * T_1$ is of sufficient duration to allow a plurality of nuclear spins in said specimen of interest to decay back to a statistically defined spin state after the last shot; and leave the spin state of the plurality of nuclear spins undisturbed when at least one of the muscular conditions is not within the acceptable range and, for all shots after a first shot, the condition that the time elapsed since the last shot is at least $N * T_1$ is not satisfied; and the set of instructions configured to provide as output at least one of an image displayed to a user, a stored image, and transmission of the image to a remote location for storing or viewing.

In one embodiment, the statistically defined spin state is an equilibrium state.

In another embodiment, the statistically defined spin state is a spin state that is a statistically similar spin state to a spin state that existed at the start of a previous shot.

In yet another embodiment, a zero flip angle shot is applied to leave the plurality of nuclear spins undisturbed.

In a further embodiment, a shot is omitted to leave the plurality of nuclear spins undisturbed.

In one embodiment, the set of instructions is configured to control the operation of the system in an iterative manner.

In another embodiment, the set of instructions is configured to control the operation of the system iteratively to take a number of shots sufficient to provide an image of the body part of the living subject.

In yet another embodiment, the body part is cardiac tissue.

In yet another embodiment, the body part is diaphragm tissue.

In still another embodiment, the value of N is approximately 5.

In yet other embodiments, the value of N is less than 5, and the plurality of nuclear spins is in a statistically similar spin state to a spin state that existed at the start of a previous shot.

According to another aspect, the invention relates to an improvement in a magnetic resonance imaging method operating on a computer-based control apparatus that controls the timing of the taking of magnetic resonance images based on a muscular state of a body part of a living subject. The improvement comprises the steps of determining whether or not a muscular condition of a body part of a living subject is within an acceptable range; determining whether or not, for all shots after a first shot, a time elapsed since the last shot was taken is at least $N*T_1$, where $T_1$ is a time constant representative of a decay rate for a specimen of interest in a magnetic resonance process and N represents a numerical value greater than one, and $N*T_1$ is of sufficient duration to allow the nuclear spins in the specimen of interest to decay back to a statistically defined spin state after the last shot; if both determining steps result in a positive outcome, permitting the taking of a magnetic resonance image (a "normal shot"); if either determining step results in a negative outcome, inhibiting the taking of a "normal shot", leaving the spin state of the nuclear spins undisturbed, and repeating the two determining steps until both outcomes are positive; and after the step of permitting the taking of a magnetic resonance image is performed, providing as output at least one of an image displayed to a user, a stored image, and transmission of the image to a remote location for storing or viewing.

In one embodiment, leaving the spin state of the plurality of nuclear spins undisturbed is accomplished by applying a zero flip angle shot.

In another embodiment, leaving the spin state of the plurality of nuclear spins undisturbed is accomplished by omitting a shot.

In one embodiment, the body part is cardiac tissue.

In yet another embodiment, the body part is diaphragm tissue.

In another embodiment, the value of N is approximately 5.

In a different embodiment, the value of N is less than 5, and the plurality of nuclear spins is in a statistically similar spin state to a spin state that existed at the start of a previous shot.

In yet another embodiment, the step of permitting the taking of a magnetic resonance image performed in an iterative manner.

In still another embodiment, the method further comprises repeating the two determining steps and the permitting step until an entire image of interest is acquired.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

We have developed a technique, called the Relaxation-Corrected ECG-Triggering and Navigator-Gating Technique, to eliminate the artifact (for example, the banding artifact in FIG. 1C, 2A and 2C) caused by variation in the condition of the spin of hydrogen in tissues that are being observed. This Relaxation-Corrected ECG-Triggering and Navigator-Gating Technique is believed to be novel because it controls for variation in the condition of spin relaxation in addition to adjusting for the motion of the cardiac and respiratory cycles.

By correcting for variation in spin relaxation occurring over the course of image acquisition, the Relaxation-Corrected ECG-Triggering and Navigator-Gating Technique eliminates a source of image artifacts, which is an additional source of bias that was not eliminated by earlier techniques, and thus the technique improves the quality of images. This improved quality can lead to improved diagnosis and therapy assessment for patients with a wide range of medical conditions.

As used herein, the acronym MR refers to magnetic resonance, the acronym MRI refers to magnetic resonance imaging, and the acronym NMR refers to nuclear magnetic resonance.

The new methodology for two-dimensional imaging significantly improves upon current ECG-triggering and navigator-gating techniques by implementing additional gating of image acquisition via synchronization of the relaxation condition of the spin of nuclei with the cardiac and respiratory cycles. This relaxation-corrected technique accomplishes improved signal acquisition by further restricting the image slices that are used for final MR images.

The Relaxation-Corrected ECG-Triggering and Navigator-Gating Technique is implemented through a software adjustment on conventional MRI scanners. Validation experiments performed at UMass Medical School, on phantoms and in vivo, have demonstrated that the technique is highly effective. The improved signal that results from this technique is illustrated in FIG. 1B, FIG. 1D, FIG. 2B, and FIG. 2D.

Figure 1A:
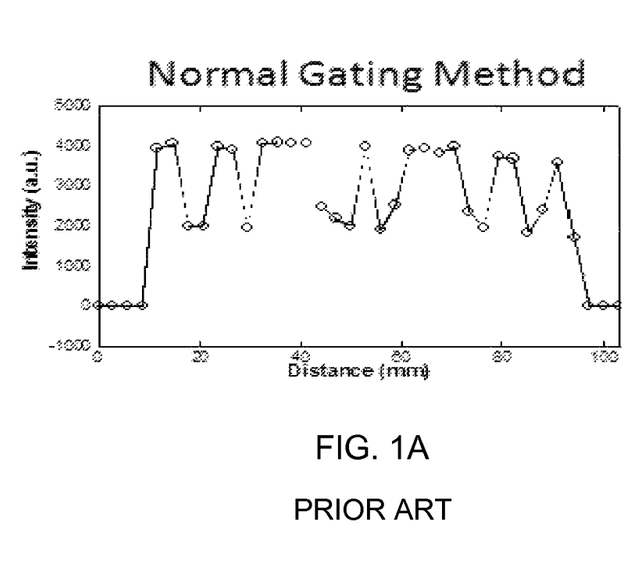
FIG. 1A is a graph showing the variation in signal intensity versus distance across a phantom as recorded using the normal (or conventional) ECG-triggering and navigator-gating method for recording MR images.

FIG. 1A is a graph showing the variation in signal intensity versus distance across a phantom as recorded using the normal (or conventional) ECG-triggering and navigator-gating method for recording MR images.

Figure 1B:
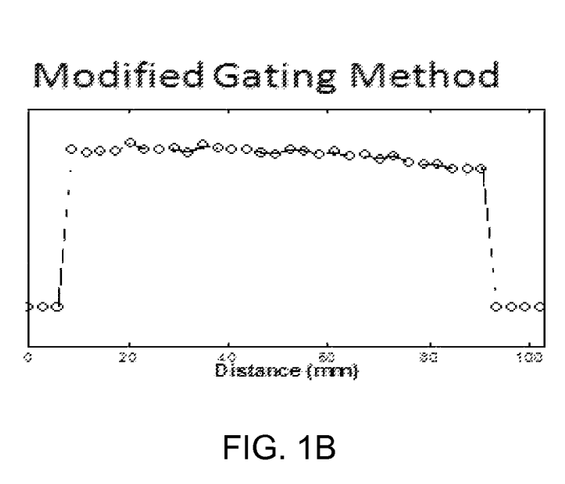
FIG. 1B is a graph showing the variation in signal intensity versus distance across the phantom as recorded using the Relaxation-Corrected ECG-Triggering and Navigator-Gating Technique according to the present description for recording MR images.

FIG. 1B is a graph showing the variation in signal intensity versus distance across the phantom as recorded using the Relaxation-Corrected ECG-Triggering and Navigator-Gating Technique according to the present description for recording MR images.

Figure 1C:
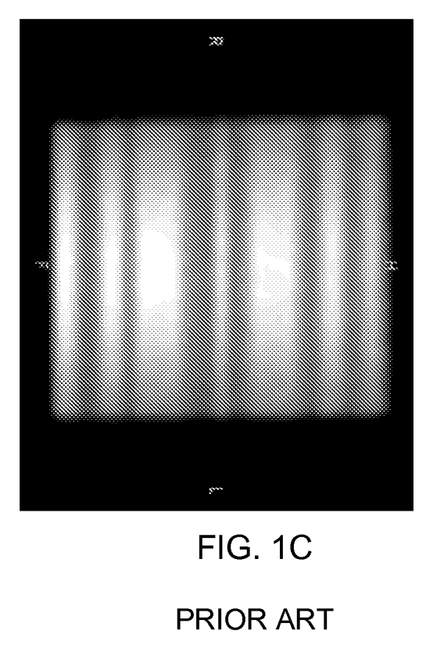
FIG. 1C is a reconstructed MR image of a phantom from the sagittal images acquired by the normal ECG-triggering and navigator-gating method.
Figure 1D:
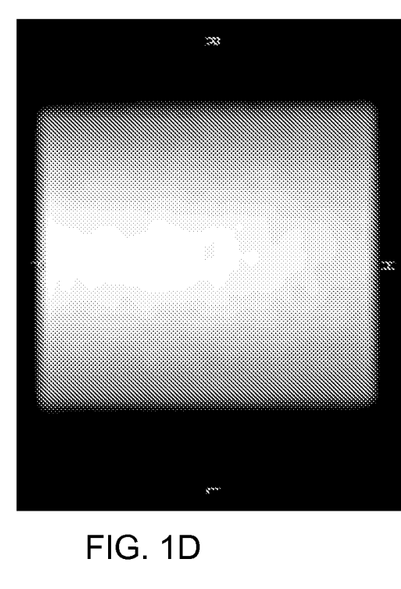
FIG. 1D is a corresponding image using the Relaxation-Corrected ECG-Triggering and Navigator-Gating Technique.
Figure 2A:
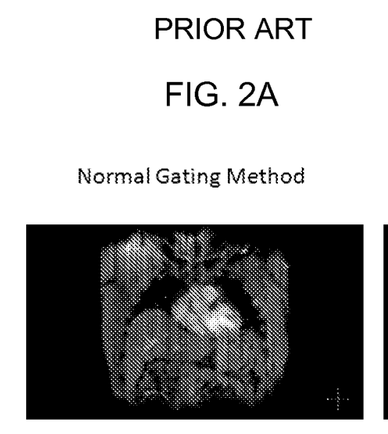
FIG. 2A is an in vivo coronal magnetic resonance image reconstructed from the sagittal images recorded using conventional ECG-Triggering and Navigator-Gating MRI techniques.
Figure 2B:
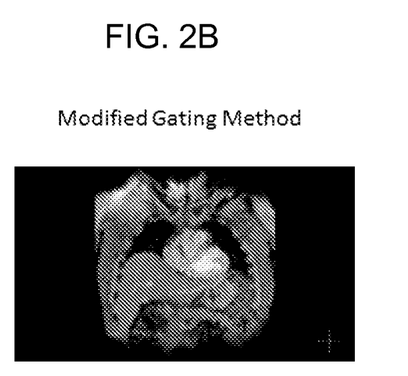
FIG. 2B is an in vivo coronal magnetic resonance image reconstructed from the sagittal images recorded using the Relaxation-Corrected ECG-Triggering and Navigator-Gating Technique.
Figure 2C:
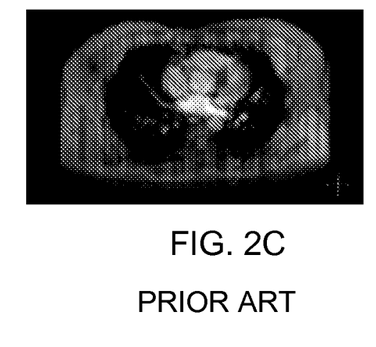
FIG. 2C is an in vivo transverse magnetic resonance image reconstructed from the sagittal images recorded using conventional ECG-Triggering and Navigator-Gating MRI techniques.
Figure 2D:
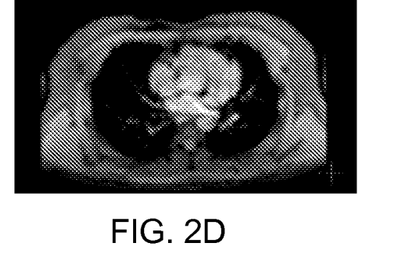
FIG. 2D is an in vivo transverse magnetic resonance image reconstructed from the sagittal images recorded using the Relaxation-Corrected ECG-Triggering and Navigator-Gating Technique.

FIG. 1C is an MR image of a phantom reconstructed from the sagittal images acquired by the normal ECG-triggering and navigator-gating method. FIG. 1D is a corresponding image using the Relaxation-Corrected ECG-Triggering and Navigator-Gating Technique. As is clearly seen, the image in FIG. 1D is significantly improved with regard to banding artifacts as compared to the image in FIG. 1C, i.e., the banding artifacts are eliminated by the Relaxation-Corrected ECG-Triggering and Navigator-Gating Technique.

The images were reconstructed from the sagittal images acquired by a M2D (Multi-2 Dimension) and single-shot TFE pulse sequence, combined with the normal ECG-triggering and navigator-gating techniques or the Relaxation-Corrected ECG-Triggering and Navigator-Gating Technique. For phantom experiments, the trigging signal was provided by the physiological simulation of the scanner and the diaphragm motion was simulated by manually moving a water phantom.

FIG. 2A, FIG. 2B, FIG. 2C, and FIG. 2D compare in vivo MR images of a human subject using the normal ECG-triggering and navigator-gating method, with images using the Relaxation-Corrected ECG-Triggering and Navigator-Gating Technique. The images in FIG. 2B and FIG. 2D produced with use of the Relaxation-Corrected ECG-Triggering and Navigator-Gating Technique are of far higher quality, with significantly reduced banding artifacts as compared to the corresponding FIG. 2A and FIG. 2C, respectively, which were recorded using conventional ECG-triggering and navigator-gating method on the same instrument.

The relaxation-corrected ECG-triggering and navigator-gating technique was validated for M2D-Turbo Field Echo (TFE) imaging of the heart. In the M2D imaging method, multiple image slices are excited one after the other. It is expected that the technique can also be adapted for other types of movement in other organs throughout the thoracic and abdominal cavities. It is expected that the technique can be applied for use with other MR imaging methods, including 3-D imaging, spiral imaging, radial imaging, multi-slice interleaved imaging, multi-shot imaging, spin-echo imaging, and coronary artery imaging.

In the Relaxation-Corrected ECG-Triggering and Navigator-Gating Technique, when the navigator pulse assessing diaphragm position occurs right before a shot (which is a condition termed a "leading navigator"), if the diaphragm is found to be out of the navigator window, the technique uses a "dummy shot" with a Flip Angle (FA) of 0° instead of a "real shot" or "normal shot." Alternatively, one can just skip a shot. This innovation keeps the spin of nuclei in the tissue being imaged at the equilibrium state until the diaphragm is found in the navigator window and a real shot is conducted. Without this correction, a real shot would change the state of the spin, creating a confound for subsequent shots. With this improvement, all the spins are kept at equilibrium before real signal acquisition is performed.

Mathematical Description

A brief explanation of NMR using hydrogen, as an example is now presented, as described in an MRI physics course (in notes by Jerry Allison, Chris Wright, and Tom Lavin, of the Department of Radiology of the Medical College of Georgia). NMR using hydrogen is well known to those of ordinary skill in the nuclear magnetic resonance arts. Atoms that contain odd numbers of protons or neutrons (or both) possess nuclear magnetic moments, whereas atoms that have even numbers of protons and neutrons have no spin and are not observed in NMR methods. Hydrogen (having one proton and no neutron), and its isotopes deuterium (one proton and one neutron) and tritium (one proton and two neutrons) all can be observed using NMR. Hydrogen is much more abundant than either deuterium or tritium, so those isotopes will not be addressed here in detail. Hydrogen is present in water ($H_2O$) and various organic compounds present in the body. One can expect that the hydrogen will provide significant NMR signals. In fact, hydrogen is used as a reference material for NMR signal, generally providing a signal that is much larger than essentially every other NMR-active nucleus. However, $^{19}F$, $^{3}He$, $^{31}P$, $^{13}C$, $^{23}Na$, $^{129}Xe$, $^{7}Li$, $^{17}O$ and other nuclei also give readily observable NMR signals and can be used for imaging and spectroscopy.

Hydrogen nuclei have only two available spin states. Hydrogen is said to have nuclear spin of ½. The two possible spin states are spin up (low energy state: parallel to applied static magnetic field) and spin down (high energy state: antiparallel to applied static magnetic field). The energy difference between the spin up and spin down states, denoted by $\Delta E = h\nu$, is directly proportional to the applied magnetic field, where h=Planck's constant ($6.62 \times 10^{-34}$ J s), and $\nu$=spin frequency (cycles/s, or Hertz). When RF energy is supplied at the resonant frequency of the nucleus, known as the Larmor frequency, the nuclei can change state between the up and down conditions. A transition from spin up to spin down absorbs energy (as the nucleus increases in energy), which a transition from spin down to spin up releases energy.

The Larmor equation, given below, describes the resonant precessional frequency of a nuclear magnetic moment in an applied static magnetic field.

$$\omega = \gamma B_o$$

where $\omega$=precessional frequency (resonant frequency), $\gamma$=gyromagnetic ratio (MHz/Tesla), and $B_o$=magnetic field (Tesla). The Larmor frequency of hydrogen in a field of 1.5 Tesla is 63.87 MHz, while the Larmor frequency of deuterium in a 1.5 Tesla field is 9.795 MHz. This resonant frequency difference makes distinguishing hydrogen from deuterium a simple matter.

Conventional RF coils and RF electronics used in MRI are tuned for a narrow band of RF frequencies. Hydrogen is commonly imaged in MRI because of its high sensitivity and abundance. To convert from imaging H to imaging another nuclear substance, one would need to employ RF coils and RF electronics that can be tuned for the alternate frequency.

According to electromagnetic theory, RF excitation can be described as a rotating magnetic field (and electric field) in the plane perpendicular to the static magnetic field $B_o$. RF excitation is produced by applying an oscillating voltage waveform to an RF exciter (transmitter) coil. The magnetic field component that rotates in the transverse plane during RF excitation is referred to as the $B_1$ magnetic field.

Frequently, the macroscopic magnetization is spiraled down until it precesses in the transverse plane (plane perpendicular to the static magnetic field). This is called a 90° flip. After a 90° flip, the macroscopic magnetization is precessing entirely in the transverse plane at the Larmor frequency and there are equal numbers of nuclei in the spin up and spin down states.

After the 90° flip, the longitudinal component of the magnetization in the direction of the static magnetic field ($B_o$) is zero. The macroscopic magnetization prior to a 90° flip is entirely longitudinal and is said to point along the "Z" axis. Following a 90° flip, magnetization is entirely transverse and is said to rotate or precess in the transverse plane defined by the "X" and "Y" axes. From the transverse magnetization state, the spin population relaxes to the thermal equilibrium magnetization condition, in which an equilibrium of up and down spins exists, as given by the well-known Boltzmann relation. A free-induction decay (FID) signal arises representing the relaxation of the transverse magnetization is induced in the RF coil.

The spin component in the direction of the static magnetic field $B_o$ returns exponentially to thermal equilibrium magnetization with rate constant $T_1$. $T_1$ is a measure of the time required to re-establish thermal equilibrium between the spins and their surroundings. $T_1$ increases as the magnetic field increases.

The mechanism behind this phenomenon can be expressed as follows. After a 90 degree RF shot is applied, the longitudinal magnetization will relax to the equilibrium state as a function of time expressed by the equation $$M(t)=Mo(1-\exp(-t/T_1))$$

where Mo is the magnetization during the equilibrium state, t is time, and $T_1$ is a time constant representative of a decay rate for a specimen in a magnetic resonance process. If t is less than about 5 times larger than $T_1$, then M(t) will not be fully relaxed. In this case, the next RF shot will result in a signal that is less than the first one. In the case of M2D heart imaging, the TR value, which is the time interval between the two shots and is decided by the heart rate, is about 1 second, which is smaller than the $T_1$ value of the heart tissue, which is about 1471 ms on a 3T scanner.

Figure 3:
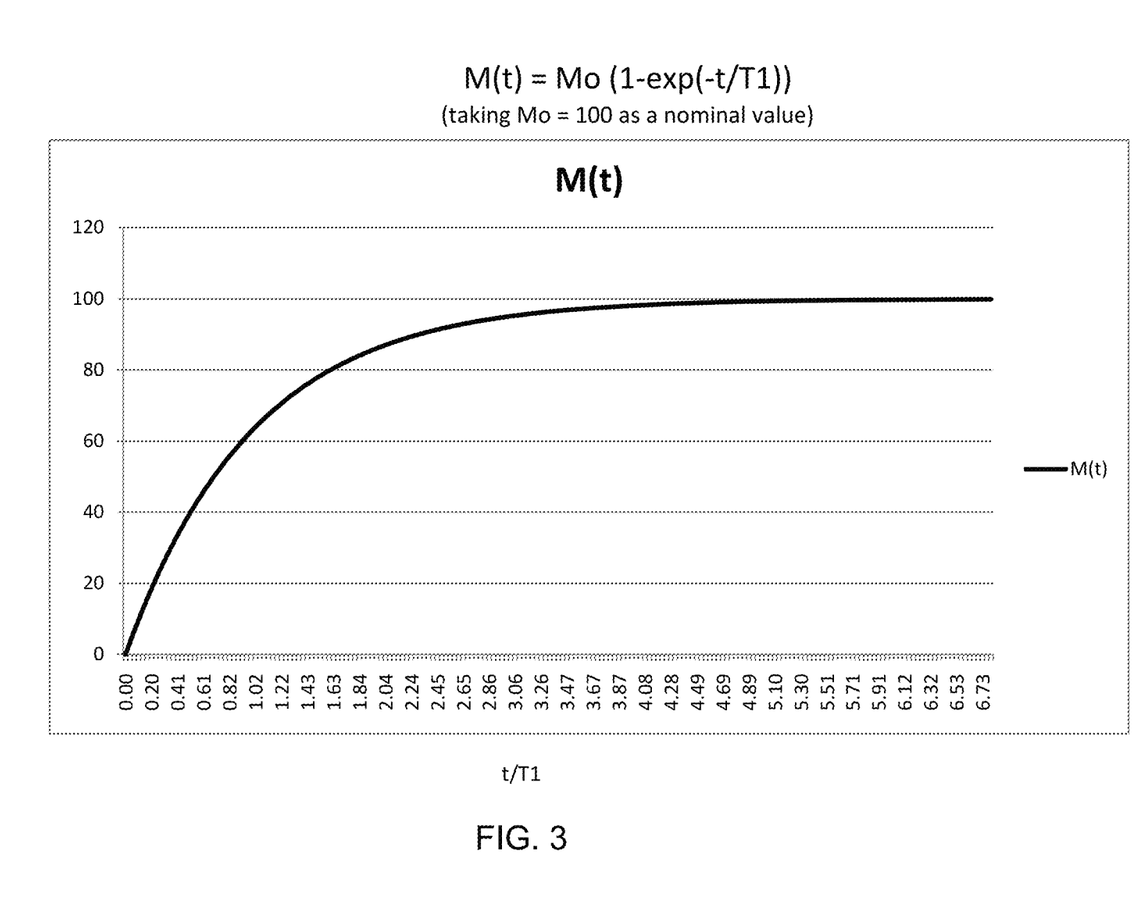
FIG. 3 is a graph showing the evolution of the magnetization M(t) with time after a 90 degree shot, in which a $T_1$ value of 1471 ms was used to simulate the relaxation of heart at 3T scanner.

FIG. 3 is a graph showing the evolution of the magnetization M(t) with time. For the purposes of illustrating the evolution of M(t), we have taken the value of Mo as being nominally 100 units. The time spacing t was taken as 200 increments of 50 milliseconds (ms) each. For heart tissue, with $T_1$=1471 ms, the units of relative time ($t/T_1$) along the x-axis range from 0/1471=0 to 10000/1471=6.7981. The x-axis labels range from 0.00 to 6.66 but several additional time unit marks are shown. As can be seen (or as can be deduced by performing the calculation of M(t)), M(t) attains the values shown in Table I.

TABLE I

| $t/T_1$ (dimensionless units) | M(t) as percentage of Mo |
|---|---|
| 1 | 63.212 |
| 2 | 86.466 |
| 3 | 95.021 |
| 4 | 98.168 |
| 5 | 99.326 |
| 6 | 99.752 |
| 7 | 99.909 |

Figure 4:
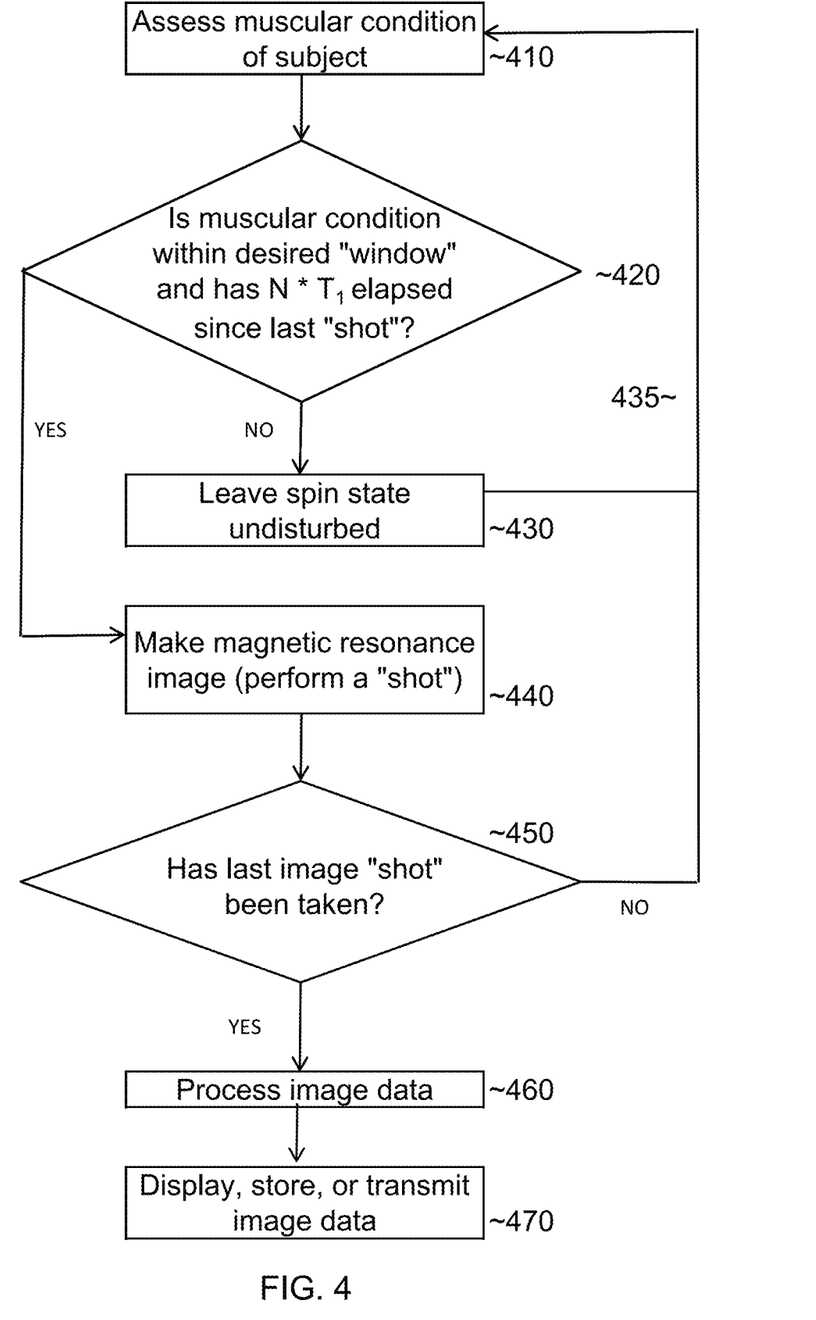
FIG. 4 is a diagram that illustrates the system-control scheme (or system-control logic) and also represents a flow diagram of the process by which the improvement in making magnetic resonance images is implemented.

FIG. 4 is a diagram that illustrates the system-control scheme (or system-control logic) and also represents a flow diagram of the process by which the improvement in making magnetic resonance images is implemented. In FIG. 4 at step 410, the muscular condition of a subject is assessed to determine if a suitable "shot" or image element can be taken, or a series of shots, in the case of a fast imaging sequence. As described hereinabove with regard to cardiac imaging, the condition of the cardiac muscles and the diaphragm muscles are taken into consideration. For making magnetic resonance images of some other part of the body, such as some other organ in the subject, other muscular condition might need to be assessed.

At step 420, a decision is taken as to whether both the necessary muscular conditions exist (e.g., that the muscular condition of the body part(s) of interest are within an acceptable range or "window") and, for all shots after a first shot, that a time long enough has elapsed since the last shot. The time that is considered to be long enough is given by $N^* T_1$, where N represents a numerical value greater than one and of sufficient size to allow the nuclear spins of interest to decay back to an equilibrium state after a shot. The numerical value N is clearly a lower bound, as waiting longer between shots (e.g., after the equilibrium is effectively attained) is also acceptable in principle. As indicated hereinabove, for cardiac tissue, N is approximately 5, but it should be understood that N does not need to be an integer. In some embodiments, N can also be less than 5, but $N^*T_1$ should be equal or similar for all shots so that the spin states of nuclei in the object being measured are in a statistically similar condition for each shot, which one can consider to be a defined spin state. In the defined spin state, a plurality of nuclear spins is in a statistically equivalent spin state (or statistically similar spin state) to a spin state that existed at the start of a previous shot.

If the outcome of the decision at step 420 is that either the muscular condition is not within the window or that the time elapse is not yet at least N * $T_1$, the flow proceeds according to the arrow marked NO that connects step 420 to step 430. At step 430, the nuclear spins are left undisturbed. This can be accomplished by applying a zero flip angle shot. Alternatively, this can be accomplished by skipping a shot. The process then follows arrow 435 back to step 410, where the condition of the subject is again assessed.

If the outcome of the decision at step 420 is that both the muscular condition is within the range or window and that the time elapsed since the last "shot" is at least $N^*T_1$, the flow proceeds according to the arrow marked YES that connects step 420 to step 440.

At step 440 the system performs a "shot" to make another magnetic resonance image (or image section) of the body portion of interest of the subject. Process flow then takes the process to step 450.

At step 450 a decision is taken as to whether the last image "shot" that is needed to prepare an image of the body part of the subject has been taken. If the result of the decision at step 450 is that the last "shot" has been taken (e.g., that sufficient images of suitable quality have been taken to allow a complete image of interest to be prepared), the image data is processed as needed at step 460, and an image (and as desired, the data representative of the image) are treated to provide at least one of an image displayed to a user, a stored image (and as may be desired or needed, stored data), and transmission of the image (and as desired or required, the image data) to a remote location for storing or viewing.

If the decision at step 450 is that the last "shot" needed to make the image of interest has not yet been taken, the system follows arrow 435 back to step 410, where the condition of the subject is again assessed, and additional image data can be taken.

Our technique is useful for the M2D signal-shot TFE method. In various embodiments of our method, the slice order could be of any kind. A preferred embodiment uses an interleaved order. It is believed that an interleaved order is advantageous to overcome the leakage of excitation. In other embodiments, K-space encoding can be any kind of order as well.

Trailing Navigator

When a navigator pulse assessing diaphragm position occurs right after a shot (a condition termed a "trailing navigator"), a different method would have to be used because the real shot was performed before the navigator was performed. In such a case, if the trailing navigator indicates the diaphragm is out of the navigator window, the data would not be used and the scanner would proceed to sampling the next slice, thus avoiding bias from the change in spin caused by the real shot that came prior to the trailing navigator. If the image data corresponding to a specific slice were omitted, data would then be re-acquired for that original slice after all other shots for all other slices were performed, because the spins would have had a chance to return to equilibrium by that time. But for the last five shots, they should be treated as the leading navigator method to save time. In some embodiments, it is expected that the leading and trailing navigator sampling will be combined, providing the most robust data in terms of controlling for both diaphragm position and spin relaxation. In this case, the method for leading navigator and trailing navigator should be combined.

Definitions

Unless otherwise explicitly recited herein, any reference to an electronic signal or an electromagnetic signal (or their equivalents) is to be understood as referring to a non-volatile electronic signal or a non-volatile electromagnetic signal.

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/ SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/ write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field-programmable array ("FPGA") chips or application-specific integrated circuits ("ASIC") chips can perform microcomputer functions, either in hardware logic, software emulation of a microcomputer, or by a combination of the two. Apparatuses having any of the inventive features described herein can operate entirely on one microcomputer or can include more than one microcomputer.

General-purpose programmable computers useful for controlling instrumentation, recording signals, and analyzing signals or data according to the present description can be any of a personal computer (PC), a microprocessor-based computer, a portable computer, or other type of processing device. The general-purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux, or of Solaris. Computational results obtained in the operation of the general-purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatuses can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware, and software for another implementation of the equivalent functionality using a different one of hardware, firmware, and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware, and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. In a magnetic resonance imaging system having a computer-based control apparatus that controls the timing of the taking of magnetic resonance images based on a muscular state of a body part of a living subject, the improvement comprising:
a set of instructions recorded on a machine-readable medium, the set of instructions when operating configured to control the operation of the system in response to two conditions to provide two mutually exclusive outcomes, so as to:
determine whether or not a muscular condition of a body part of a living subject is within an acceptable range;
permit the taking of a magnetic resonance image (a "shot") when both said muscular condition is within said acceptable range and when, for all shots after a first shot, an elapsed time since the last shot was taken is at least $N * T_1$, where $T_1$ is a time constant representative of a decay rate for a specimen of interest in a magnetic resonance process and N represents a numerical value greater than one, and $N * T_1$ is of sufficient duration to allow a plurality of nuclear spins in said specimen of interest to decay back to a statistically defined spin state after the last shot; and
apply a zero flip angle shot to leave said spin state of said plurality of nuclear spins undisturbed when at least one of said muscular conditions is not within said acceptable range and, for all shots after a first shot, said condition that said time elapsed since said last shot is at least $N * T_1$ is not satisfied; and
said set of instructions configured to provide as output at least one of an image displayed to a user, a stored image, and transmission of an image to a remote location for storing or viewing.

2. The magnetic resonance imaging system of claim 1, wherein said statistically defined spin state is an equilibrium state.

3. The magnetic resonance imaging system of claim 1, wherein said statistically defined spin state is a spin state that is a statistically similar spin state to a spin state that existed at the start of a previous shot.

4. The magnetic resonance imaging system of claim 1, wherein said set of instructions is configured to control the operation of the system in an iterative manner.

5. The magnetic resonance imaging system of claim 1, wherein said set of instructions is configured to control the system to take a number of shots sufficient to provide an image of said body part of the living subject.

6. The magnetic resonance imaging system of claim 1, wherein said body part is cardiac tissue, a muscular state of said cardiac tissue being determined using an ECG-triggering technique and an acceptable range for said ECG-triggering being a heart in diastole.

7. The magnetic resonance imaging system of claim 1, wherein said body part is diaphragm tissue, a muscular state of said diaphragm tissue being determined using a navigator-gating technique and an acceptable range for said navigator-gating technique being said diaphragm tissue within a navigator window.

8. The magnetic resonance imaging system of claim 1, wherein said value of N is approximately 5.

9. The magnetic resonance imaging system of claim 1, wherein said value of N is less than 5, and said plurality of nuclear spins is in a statistically similar spin state to a spin state that existed at the start of a previous shot.

10. In a magnetic resonance imaging method operating on a computer-based control apparatus that controls the timing of the taking of magnetic resonance images based on a muscular state of a body part of a living subject, the improvement comprising the steps of:
determining whether or not a muscular condition of a body part of a living subject is within an acceptable range;
determining whether or not, for all shots after a first shot, a time elapsed since the last shot was taken is at least $N * T_1$, where $T_1$ is a time constant representative of a decay rate for a specimen of interest in a magnetic resonance process and N represents a numerical value greater than one, and $N * T_1$ is of sufficient duration to allow a plurality of nuclear spins in said specimen of interest to decay back to a statistically defined spin state after the last shot;
if both determining steps result in a positive outcome, permitting the taking of a magnetic resonance image (a "normal shot");
if either determining step results in a negative outcome, inhibiting the taking of a "normal shot", leaving said spin state of said nuclear spins undisturbed by applying a zero flip angle shot, and repeating the two determining steps until both outcomes are positive; and after said step of permitting the taking of a magnetic resonance image is performed, providing as output at least one of an image displayed to a user, a stored image, and transmission of an image to a remote location for storing or viewing.

11. The magnetic resonance imaging method of claim 10, wherein said body part is cardiac tissue, a muscular state of said cardiac tissue being determined using an ECG-triggering technique and an acceptable range for said ECG-triggering being a heart in diastole.

12. The magnetic resonance imaging method of claim 10, wherein said body part is diaphragm tissue, a muscular state of said diaphragm tissue being determined using a navigator-gating technique and an acceptable range for said navigator-gating technique being said diaphragm tissue within a navigator window.

13. The magnetic resonance imaging method of claim 10, wherein said value of N is approximately 5.

14. The magnetic resonance imaging method of claim 10, wherein said value of N is less than 5, and said plurality of nuclear spins is in a statistically similar spin state to a spin state that existed at the start of a previous shot.

15. The magnetic resonance imaging method of claim 10, wherein said step of permitting the taking of a magnetic resonance image performed in an iterative manner.

16. The magnetic resonance imaging method of claim 10, further comprising repeating the two determining steps and the permitting step until an entire image of interest is acquired.

* * * * *